(12) United States Patent
Brockman et al.

(10) Patent No.: US 10,588,660 B2
(45) Date of Patent: Mar. 17, 2020

(54) ACCESS CANNULA ASSEMBLY WITH A STYLET THAT INCLUDES A FLEXIBLE LOCK ARM

(71) Applicant: Stryker Corporation, Kalamazoo, MI (US)

(72) Inventors: Christopher Scott Brockman, Kalamazoo, MI (US); Kevin Kuiper, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 176 days.

(21) Appl. No.: 15/568,123

(22) PCT Filed: Apr. 21, 2016

(86) PCT No.: PCT/US2016/028635
§ 371 (c)(1),
(2) Date: Oct. 20, 2017

(87) PCT Pub. No.: WO2016/172335
PCT Pub. Date: Oct. 27, 2016

(65) Prior Publication Data
US 2018/0146982 A1  May 31, 2018

Related U.S. Application Data

(60) Provisional application No. 62/150,999, filed on Apr. 22, 2015.

(51) Int. Cl.
*A61B 17/34* (2006.01)
*A61B 10/02* (2006.01)

(52) U.S. Cl.
CPC ...... *A61B 17/3421* (2013.01); *A61B 10/0233* (2013.01); *A61B 2017/347* (2013.01)

(58) Field of Classification Search
CPC ............ A61B 10/0233; A61B 17/3421; A61B 17/3494; A61B 2017/347
See application file for complete search history.

(56) References Cited

U.S. PATENT DOCUMENTS

| 4,609,370 | A | * | 9/1986 | Morrison | ........... | A61B 17/3401 600/567 |
| 4,838,282 | A | | 6/1989 | Strasser et al. | | |
| 4,938,746 | A | * | 7/1990 | Etheredge, III | .... | A61J 15/0007 128/200.26 |
| 5,336,191 | A | * | 8/1994 | Davis | ................. | A61B 10/0283 604/165.01 |

(Continued)

OTHER PUBLICATIONS

International Search Report for Application No. PCT/US2016/028635 dated Jun. 2, 2016, 3 pages.

*Primary Examiner* — Jocelin C Tanner
(74) *Attorney, Agent, or Firm* — Howard & Howard Attorneys PLLC (57) ABSTRACT

A cannula assembly including a cannula and a stylet that is removably fitted in the cannula. A lock selectively holds the stylet to the cannula so the stylet rotates in unison with the cannula. The lock is configured so that the force applied to release the lock results in the subsequent rotation of the stylet relative to the cannula. Methods of disengaging a lock assembly releasably coupling a stylet handle secured to a stylet and a cannula handle secured to a cannula are also provided.

20 Claims, 5 Drawing Sheets

(56) References Cited

U.S. PATENT DOCUMENTS

| | | | |
|---|---|---|---|
| 6,312,394 B1 | 11/2001 | Fleming, III | |
| 6,554,778 B1 | 4/2003 | Fleming, III | |
| 2003/0171718 A1* | 9/2003 | DeLegge | A61B 17/3415 604/164.01 |
| 2004/0162559 A1* | 8/2004 | Arramon | A61B 17/3417 606/62 |
| 2007/0010843 A1 | 1/2007 | Green | |
| 2008/0262383 A1 | 10/2008 | Routhier et al. | |
| 2009/0024056 A1* | 1/2009 | Bacon | A61B 10/0233 600/567 |
| 2010/0036381 A1 | 2/2010 | Vanleeuwen et al. | |
| 2012/0059380 A1* | 3/2012 | Deangelo | A61B 17/8819 606/94 |

* cited by examiner

ACCESS CANNULA ASSEMBLY WITH A STYLET THAT INCLUDES A FLEXIBLE LOCK ARM

CROSS-REFERENCE TO RELATED APPLICATIONS

The present application is the National Stage of International Patent Application No. PCT/US2016/028635, filed on Apr. 21, 2016, which claims priority to and all the benefits of U.S. Provisional Patent Application No. 62/150,999, filed on Apr. 22, 2015, each of which is hereby expressly incorporated herein by reference in its entirety.

FIELD OF THE INVENTION

This invention relates generally to an access cannula assembly that includes both an access cannula and a stylet. The assembly of this invention further includes a lock assembly that holds the stylet to the cannula when these two components are subjected to different forces and that is able to quickly unlock the stylet from the cannula.

BACKGROUND OF THE INVENTION

An access cannula assembly, as implied by its name, is a medical/surgical tool used to form a portal into tissue within the patient. It is typically desirable form this portal so a procedure can be formed on the tissue adjacent the distal end of the portal. For example, one type of procedure for which it is desirable to form such a portal is biopsy procedure. In a biopsy procedure, once the portal is formed, a biopsy instrument is inserted in the portal. This biopsy instrument is used to retrieve a sample of the tissue. The retrieved tissue is then studied to determine the pathology of the tissue in the patient. Another type of procedure in which it is desirable to form a portal into a patient is a vertebroplasty procedure. A vertbroplasty procedure is a procedure that is performed on a fractured vertebral body. In this procedure, the access cannula is used to define a portal or passageway into a fractured vertebral body. Once the portal is formed, a stabilizing cement is introduces through the portal into the vertebral body. The cement, upon hardening, holds the fractured sections of the vertebra together. The holding together of these portions of the vertebra stabilizes the fracture to reduce the pain resulting from the fracture.

Some access cannula assemblies are designed specifically to create an opening into hard tissue, bone. This type of assembly typically includes two basic components: the actual cannula; and a stylet. The cannula is the tube like structure. The lumen or bore that extends through the cannula functions as the portal to the tissue for which access is required to perform the intended medical or surgical procedure. The stylet is often a solid rod. During the insertion of the access cannula assembly into the bone, the stylet is removably disposed in the cannula bore. The stylet is further formed to have a pointed tip. More particularly, the tip has a geometry that facilitates the driving of the stylet through the bone. The components forming an access cannula assembly are further formed so that when the stylet is seated in the cannula, the tip typically extends distally forward of the end of the cannula. Both the access cannula and tip are formed with handles. The handles facilitate the grasping of these components.

An access cannula assembly used to form a portal into bone into is typically driven into the bone and overlying soft tissue with an axial force that is applied against at least one of the cannula handle or the stylet handle. During this process the tip of the stylet functions as a drill bit or wedge that separates the tissue so the cannula can advance. The shaft of the stylet provides mechanical strength to the assembly so the cannula does not collapse under exposure to an axial load.

This force used to insert the assembly may be the simple manual force applied with the palm of the hand. In a variation on this technique, the assembly is both pushed against the bone and rotated. The rotation causes the stylet tip to drill into the tissue. Alternatively, a practitioner may use a mallet like device to drive the assembly into the bone.

Regardless of the method used to drive the access cannula into the bone, the stylet, more typically, the tip, is subjected to a greater resistive force than the resistive force to which the cannula is exposed. In response to the uneven application of these forces, the stylet tip can start to retract proximally such that the tip retracts into the cannula bore. If this event occurs, to continue the insertion process, there is a need to momentarily provide an additional quantum of force to the stylet and only the stylet in order to drive the tip forward of the cannula. Having to add this sub-step to the insertion process can increase the overall time it takes to perform the insertion process. Moreover, having to interrupt the insertion process to have to so reset the position of the stylet relative to the access cannula can interrupt the flow of the insertion process.

To minimize, if not eliminate, the instances of having to so reset the position of the stylet relative to the cannula, an access cannula assembly typically includes a lock assembly that releasably holds the stylet to the cannula. A lock assembly often consists of providing either the stylet handle or the cannula handle with one or more tabs. The other of the cannula handle or stylet handle with one or more voids for removably receiving the tabs. The components are designed so there is an interference fit between the tabs and void-defining features of the complementary handle. During the process of inserting the access cannula into the bone, the interference fit hold the tabs in the complementary voids. The tab-in-void seating is designed to reduce the likelihood that, as force is applied to either the cannula or the stylet, these components move independently from each other. Once the access cannula is at the desired location, the lock assembly is released. This allows the stylet to be withdrawn from the access cannula. The cannula bore is then clear to receive the next instrument or compound the practitioner wants to introduce into the site to which the cannula is directed.

Lock assemblies integral with many access cannula assemblies work reasonably well under many circumstances. However, in some situations, known cannula assembly lock assemblies may have a less than desirable performance. For example, one known cannula assembly has tabs that project radially outwardly from the handle integral with the stylet. These tabs extend into slots formed in the cannula handle. This type of lock can have a less than desired performance when the access cannula assembly with which the assembly is integral is twisted into bone. During this type of insertion process, as a result of the stylet being subjected to more resistive torque than the interference fit holding the tabs, the cannula handle may rotate free of the stylet lock tabs. Further, once the access cannula is positioned at the target location, the stylet tip may be firmly embedded in the adjacent bone. To free the stylet it is necessary to apply a twisting force, a torque, to the stylet. This force must be sufficient to overcome the both the resistance of the interference fit and the resistance of the bone. This type of access cannula presents a stylet handle that has a relative small area to the practitioner. This small sized handle can make it difficult to exert the necessary removal torque.

In a variation of this type of access cannula, the smaller diameter stylet handle is simply threaded to the larger sized access cannula. Again, during a twisting insertion process, due to the resistance of the bone overcoming the interference of the interference fit, the lock can disengage. This type of access cannula also has the disadvantage of the above described tab-in-void space lock. The relatively small size of the stylet handle can make it difficult to correctly apply the force required to disengage the lock and withdraw the stylet.

Another known cannula assembly includes a stylet with a handle that extends over the cannula handle. Lock tabs integral with the stylet handle project downwardly from this handle. These lock tabs extend into underlying slots formed in the cannula handle. During the twisting in of a cannula assembly with type of lock, care must be taken to rotate both handles simultaneously. If the cannula and stylet are not rotated simultaneously, the rotation of the stylet relative to the cannula can result in the unintended disengagement of the lock.

Access cannula assembles with locks designed to substantially eliminate the likelihood of unintended disengagement are available. The lock integral with this type of access cannula assembly often include a latch component that is flexible. A disadvantage of the known version of this type of assembly is that, to withdraw the stylet, it is necessary to first retract the stylet proximally. During a procedure debris, such as bone dust, can become entrained in the narrow space between the stylet and the inner wall of the cannula. These debris can impede the proximal withdrawal of the stylet.

Further, sometimes the tip of the stylet may be embedded in bone. One relatively easy means to free the tip from the bone is to rotate the stylet to break up the bone around the tip. However, since to withdraw the stylet of the above-described assembly, it is necessary to first displace the stylet longitudinally, it may not be possible to so rotate the stylet. This can make it difficult to free the tip from the bone.

SUMMARY OF THE INVENTION

This invention is related to a new and useful access cannula assembly for creating a portal to subcutaneous tissue. The access cannula assembly of this invention is especially useful for creating a portal into hard tissue such as bone.

The assembly of this invention includes an access cannula, a stylet and a lock that releasably holds the stylet to the cannula. The lock holds the stylet to the cannula when the bone exposes the stylet to a high resistive force. This resistive force is applied either axially, along the longitudinal axis of the cannula and/or rotationally, around the longitudinal axis of the cannula. The lock of the access cannula of this invention is further designed so that, once the access cannula is at the target location, the lock is relatively easy to move to the disengaged state. Once the lock is disengaged, the lock facilitates the relatively easy retraction of the stylet out of the cannula.

The access cannula of this invention includes a lock that has an arm that extends radially outwardly from the handle integral with the stylet. One end of the arm is flexibly attached to the stylet handle. The opposed end of the arm, the free end of the arm, is positioned such that the practitioner can press this end of the arm so as to flex the arm relative to the rest of the stylet handle. The cannula handle and arm integral with the stylet handle have complementary features. These features are constructed so that when the stylet handle arm is in the normal unflexed state, the surfaces engage. The engagement of these surfaces holds the stylet to the cannula so these components move as a single unit.

In many versions of this invention, the arm is formed to have at least two segments that are angled relative to each other. In some versions of the invention, the arm has three segments. A first segment is attached to the stylet handle, a second segment is arranged to engage the cannula handle. A third segment is the segment that is manually pressed to cause the flexure of the arm. The second segment of the arm is able to flex relative to the first segment of the arm.

In some versions of the invention, the arm is provided with a tab that projects outwardly from a surface of the arm. The tab seats in a complementary slot formed in the cannula handle. The arm tab and slot-defining surface of the cannula handle are the complementary features of the cannula and stylet that engage to hold the stylet to the handle.

The lock may include other complementary components that hold the stylet to the cannula. In some versions of the invention, the cannula handle is provided with a stop. The stop is located adjacent the stylet arm. The stop is positioned so that if the stylet undergoes unintended rotation relative to the cannula, the arm abuts the stop. The abutment of the arm against the stop prevents movement of the arm relative to the rest of the stylet handle that could result in unintended disengagement of the lock.

When it is time to remove the stylet from the cannula, the practitioner presses a finger or thumb against the stylet handle and the other of the finger or thumb of the same hand against the stylet handle arm. Owing to the stylet handle arm being spaced from rotational axis of the stylet, the practitioner, using this digit force alone applies torque to the stylet arm. This torques is sufficient to both flex the arm so as to cause the disengagement of the lock and to, in opposition of the resistive torque acting against the stylet tip, rotate the stylet. This disengagement of the lock followed rapidly by the rotation of the stylet facilitates the quick removal of the stylet from the cannula.

BRIEF DESCRIPTION OF THE DRAWINGS

The invention is pointed out with particularity in the claims. The above and further features and benefits of this invention are understood from the following Detailed Description taken in conjunction with the accompanying drawings in which:

DETAILED DESCRIPTION

Figure 1:
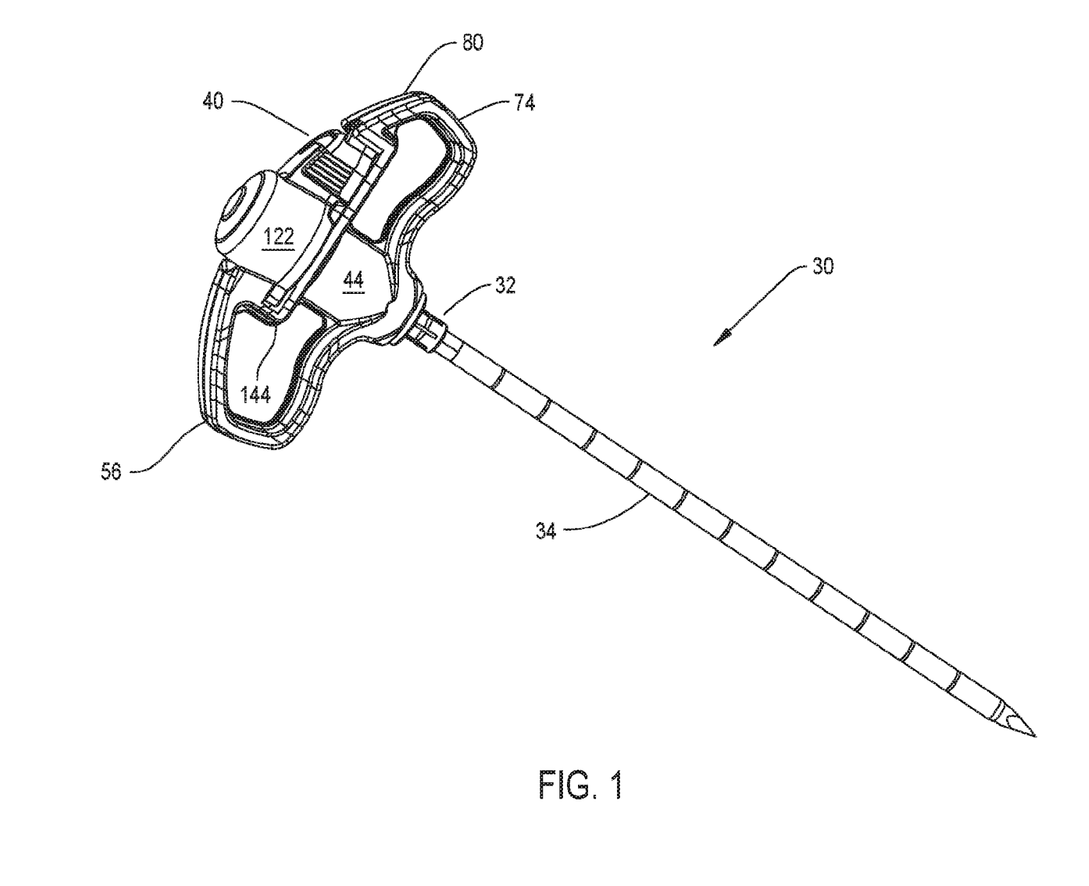
FIG. 1 is a perspective view of the access cannula of this invention.

An access cannula assembly 30 of this invention is now generally described by reference to FIGS. 1 and 2. Assembly 30 includes a cannula 32 and a stylet 110. The stylet 110 is removably inserted in the cannula 32. A lock assembly, the components of which are discussed below, removably holds the stylet 110 in the cannula 32 so the two components, when locked together, are a single piece assembly.

Cannula 32 includes a tube like cannula body 34. Body 34 defines an axially extending bore 36, seen in phantom in FIG. 3. A handle 40, best seen in FIGS. 2-5, extends around and above the proximal end of cannula body 34. ("Proximal" is understood to mean towards the practitioner using the assembly 30; away from the site to which the assembly is applied. "Distal" is understood to mean away from the practitioner, towards the site to which the assembly 30 is applied.) Handle 40 has a cylindrical neck 42 that forms the distal end of the handle. Above neck 42, handle 40 is formed to have cylindrical core 44. Core 44 has an outer diameter greater than that of neck 42. The distal end of the cannula body 34 is contained with the handle neck 42 and core 44. In the illustrated version of the invention a triangular shaped icon 46 is formed with the core 44 and extends outwardly from one side of the core. Handle 40 is formed so that the apex of icon 46 points downwardly, towards the distal end of the cannula body 34.

Cannula handle 40 is further formed to have a rectangular plate 50 that is disposed above core 44. Plate 50 lies in a plane that is perpendicular to the proximal to distal longitudinal axis through the core 44. While the plate 50 is integral with the core 44, the plate is not symmetrically arranged around the proximal-to-distal longitudinal axis through the core. On one side of core 44, plate 50 extends further away from the longitudinal axis of the core than on the opposed side. Plate 50 is formed with an opening 52 that is centered on the longitudinal axis of core 44. Opening 52 leads into the core 44 and, more particularly, into the open end of the cannula body 34 disposed in the core. Cannula handle 40 is further formed to have a stop 54 that projects upwardly from the proximally directed face of plate 50. Stop 54 projects upwardly from the section of the plate that extends furthers away from the core. The stop 54 is located adjacent a side edge of the plate. Stop 54 is generally in the shape of a truncated triangle. The base of stop 54 extends upwardly from the edge of plate 50. The opposed apex of the stop is directed to the opposed edge of the plate 50. Stop 54 is also formed to have a face 55 that cuts off one vertex of the stop. Cannula handle 40 is formed so that face 55 is directed away from the center axis of handle core 44. One of the faces of the stop 54, face 53, that give the stop the generally triangular appearance, angles away from face 55 towards plate opening 52.

Figures 3, 4:
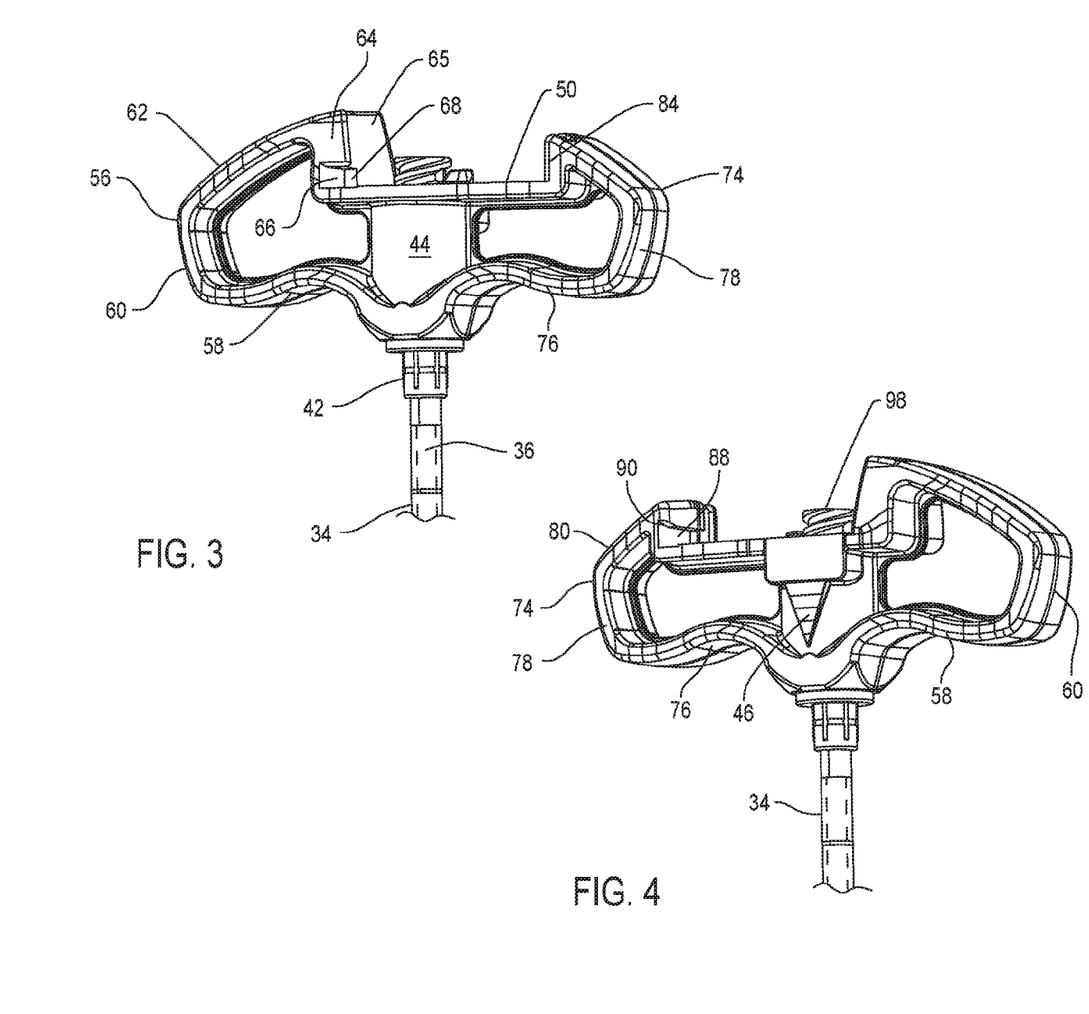
FIG. 3 is a perspective view of one side of the cannula handle.
FIG. 4 is a perspective view of the opposed side of the cannula handle.
Figure 5:
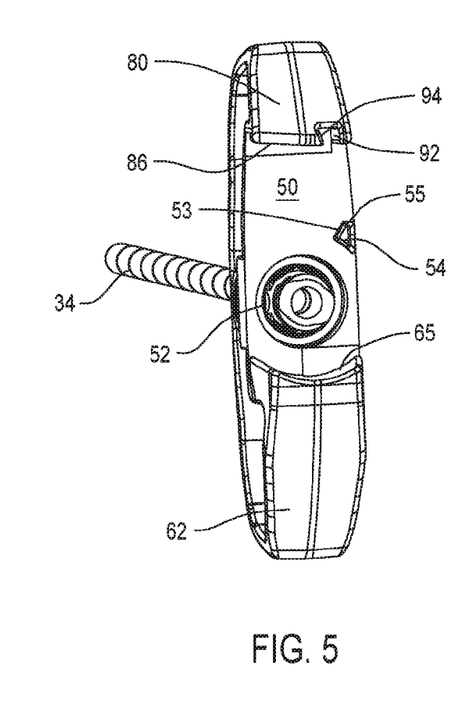
FIG. 5 is a perspective view of the top of the cannula handle.

The cannula handle 40 is further formed to have two diametrically opposed arms 56 and 74. Arms 56 and 74 extend outwardly from the core 44. Each arm 56 and 74 has a lower section, sections 58 and 76, respectively. Arm sections 58 and 76 extend outwardly from the distal section of core 44. Each arm section 58 and 76 has a profile with a wave shape designed to accommodate the proximal phalanx of a finger. Arm sections 58 and 76 are essentially identical in shape. A middle section, sections 60 and 78, respectively, extends proximally upward from the free end of each arm distal section 58 and 76. Arm middle sections 60 and 78 are essentially identical in shape. A proximal section 62 extends upwardly and inward from middle section 60 of arm 56. The proximal section 62 extends towards and above the end of plate 50 located closest to core 44. A web 64 extends downwardly from the end of arm proximal section 62 to the adjacent end of plate 50. Web 64 has a curved face 65. The center of the curvature of face 65 is the extension of the longitudinal axis through the core 44. Handle 40 is further formed so that web 64 is formed to define a closed end notch 66. Notch 66 is located immediately above plate 50. The notch 66 has an opening adjacent one side of the plate. Notch 66 only extends partially through the web. Seen only in FIG. 3 is the surface 68 internal to the web perpendicular that extends inwardly from web face 65 and perpendicular to plate 50 that defines the closed end of notch 66 disposed in the web 64.

Arm 74 includes a proximal section 80 that extends upwardly and inwardly from the proximal end of arm middle section 78. Arm proximal section 80 extends towards and terminates above the end of plate 50 spaced from core 44. A web 84 extends between the arm proximal section 80 and the underlying end of plate 50. Web 84 has a face 86 only the edge of which is identified in FIG. 5. Web face 86 is opposed to web face 65. Handle 40 is formed so that web 84 has a closed end notch 88. Notch 88 opens from the side of the handle opposite the side from which notch 66 opens. Relative to the longitudinal to distal axis through the core, notch 88 has a longer angular length than notch 66. Adjacent the open end of the notch web 84 is formed with a tapered surface 90 that defines the open end of notch 88. As a consequence of the presence of surface 90, the top to bottom height of notch 88 adjacent the opening of the notch is slightly greater than the height of the notch inward of this opening. Web 84 is formed to have a slot 92 that also extends inwardly from web face 86. Slot 92 has a major axis that is perpendicular to the major axis of notch 88. The web 84 is formed so that slot 92 extends upwardly from the closed end of notch 88 to the proximally directed end of web 84. Notch 88 and slot 92 thus collectively define an opening that extends the entire proximal to distal length along web face 86. The handle 40 is further formed such that the interior surface 94 of the handle that defines the side of slot 92 closest to core 44 is located on a plane that is not parallel to the end-to-end longitudinal planes along the plate 50. The edge of surface 94 is identified in FIG. 5. Instead, handle 44 is formed so that as surface 94 extends inwardly from web face 86, the surface extends towards the longitudinal plane through the plate that intersects the proximal-to-distal longitudinal axis through the core 44.

Cannula handle 40 is further formed to have fitting 98. Fitting 98 extends upwardly from core 44. The fitting 98 extends outwardly from plate opening 52. Fitting 98 is dimensioned to receive a coupling associated with a complementary conduit (conduit and conduit fitting not illustrated). The fitting 98 opens into the bore 36 internal to the cannula body 34. Fitting 98 is provided so that, after the cannula 32 is positioned, a practitioner can attach the conduit to the fitting. This facilitates the injection of therapeutic and diagnostic agents through the cannula bore 36 into the tissue adjacent the open end of the cannula 32.

Figure 2:
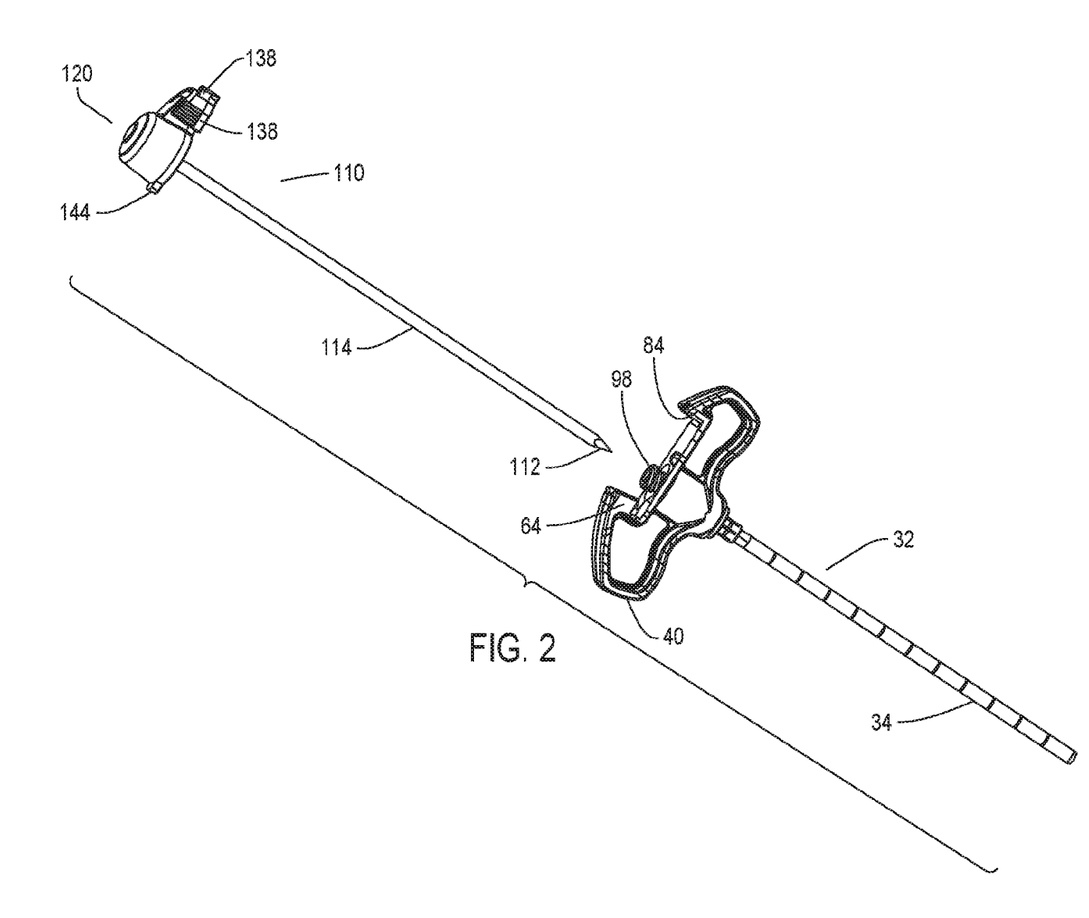
FIG. 2 is an exploded view of how the stylet is seated in the cannula.
Figure 6:
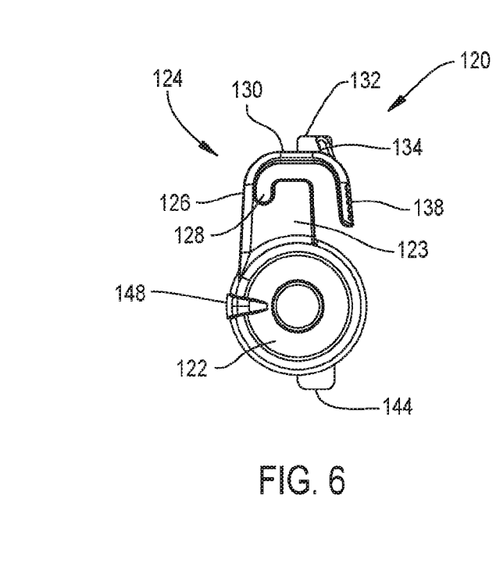
FIG. 6 is a top plan view of the stylet handle.

Stylet 110, now described by reference to FIGS. 1, 2 and 6, includes a cylindrically shaped shaft 114 as seen in FIG. 2. Shaft 114 is dimensioned to seat in the bore (36) internal to the cannula tube 34. At the distal end, shaft 114 is shaped to have a pointed tip 112. In many versions of the invention tip 112 has a geometry that facilitates using the tip piercing and penetrating both soft and hard tissue. The geometry of tip 112 is not part of the present invention.

A handle 120 is disposed over the proximal end of the shaft 114. Handle 120 has a head 122 that is generally cylindrical in shape. Head 122 is coaxial with stylet shaft 114. Head 122 has a diameter greater than that of shaft 114. More particularly, the components forming assembly 30 are designed so that that when stylet 110 is seated in cannula 32, the outer surface of handle head 120 has at least some clearance between the adjacent curved face 65 of cannula handle 40.

In the depicted version of the invention, handle head 122 has a diameter that is approximately 1 to 2 mm greater than the width across plate 50 integral with the cannula handle. When stylet 110 is seated in the cannula 32, stylet handle head 122 extends a short distance outwardly from the underlying plate 50 integral with the cannula handle 40.

The stylet handle 120 is further formed to have a shoulder 123. Shoulder 123 projects outwardly from one section of handle 120. More particularly, the assembly 30 is constructed so that when the stylet 110 is seated in the cannula 32, one side of shoulder 123 is essentially coplanar with the side edge of the underlying plate 50 integral with the cannula handle 40.

An arm 124, also part stylet handle 120, extends away from shoulder 123. Arm 124 has three sections. A first section, base 126, extends outwardly from the proximal directed face of the shoulder 123. More particularly, the base 126 extends outwardly from the side of the shoulder that is essentially coplanar with the side edge of plate 50. In the illustrated version of the invention, handle 120 is formed to define a gap 128 that extends between a concealed face of arm base 126 and an adjacent section of the shoulder 123. The second section of the arm is intermediate section 130. Intermediate section 130 extends perpendicularly from the free end of the base 126. The third section of arm 124 is the outer section, section 138. Arm outer section 138 extends perpendicularly from the intermediate section back towards handle head 122. Arm base and outer sections 126 and 138, respectively, are thus approximately to each other.

Two tabs extend outwardly from the outer surface of arm intermediate section 130. A first tab, tab 132, is rectangular in shape and extends outwardly from immediately above the bottom surface of the arm 124. The bottom surface of arm 124 is understood to be the surface of the arm that faces plate 50. Tab 132 is dimensioned to slidably move in notch 88 formed in web 84. The second tab, tab 134, intersects tab 132. Tab 134 is located adjacent the bend between arm intermediate section 130 and outer section 138. More particularly, tab 134 is located so that when tab 132 is located adjacent the surface internal to web 84 that defines the closed end of notch 88, tab 134 is seated in slot 92. Stylet handle 120 is further formed so that the while the tab 134 extends outwardly from arm intermediate section 130 the plane along which the tab 134 so extends is not perpendicular to the adjacent surface of the arm intermediate section. More particular, the plane along which tab 134 extends outwardly is angled such that, as the tab extends outwardly, the tab extends toward the end of the intermediate section 130 attached to the base section 128.

Stylet handle 120 is formed with a third tab, tab 144. Tab 144 projects outwardly from above the base of handle head 122. The base of the handle head 122 is understood to be the surface of the head disposed against cannula handle plate 50. Tab 144 is positioned so as to be arcuately closer to the arm outer section 138 than the section of shoulder 123 from which arm base 126 extends. In some versions of the invention, stylet handle 120 is further formed so that, as seen in FIG. 6, tabs 132 and 144 have end faces that are both coplanar and are within 2 mm if not the proximal-to-distal longitudinal through the shaft. The stylet handle 120 is shaped so that tab 144 is able to rotate into notch 66 formed in the cannula handle 40.

An icon 148 extends outwardly from handle head 122. Stylet icon 148 is formed on head 122 so that when the stylet 110 is locked to cannula 32, stylet icon 146 is aligned with cannula icon 46. In some versions of the invention icon 148 may also facilitate alignment of the stylet tip 112 with the tissue into which the tip is to be inserted.

Cannula assembly 30 of this invention is readied for use by inserting the stylet 110 in the cannula 32. Stylet shaft 114 is inserted through cannula fitting 98 and core 44 into the bore 36 internal to cannula body 34. Owing to the dimensioning of the components forming assembly 30, stylet tip 112 extends distally forward of the distal end of the cannula body 34. During this process, stylet handle 120 has a rotational orientation relative to cannula handle 40 that is counterclockwise to the orientation of these two components as seen in FIG. 8.

Figure 7:
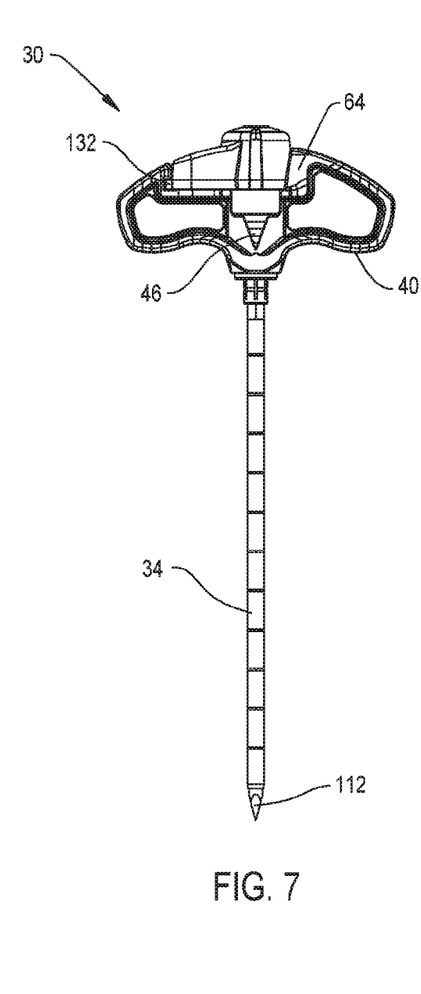
FIG. 7 is a side plan view of the assembly when the stylet is seated in the cannula.
Figure 8:
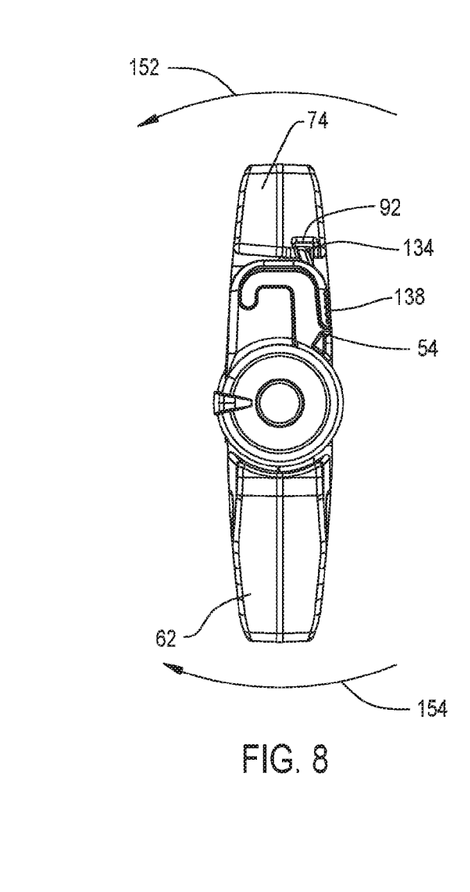
FIG. 8 is a top plan view of the cannula and stylet of the assembly of this invention when the lock is in the engaged state.

Stylet 110 is locked to cannula 32 by rotating the stylet so stylet handle 120 has the rotational orientation relative to the cannula handle as seen in FIG. 8. More particularly, stylet handle 120 is rotated clockwise, in the direction of arrow 154 of FIG. 8. As a result of this rotation of the handle 120, the free end of arm outer section 138 rotates against the adjacent angled surface 53 of stop 54. The abutment of the arm outer section 138 against stop surface 53 results in the arm middle section 130 being pushed towards web face 86. This results in the stylet handle tab 134 being pushed into the cannula handle slot 92. Simultaneously, the rotation of stylet handle 120 rotates tab 132 into cannula handle notch 88 as seen in FIG. 7. Also, stylet tab 144 is rotated in cannula handle notch 66 as seen in FIG. 2. Once stylet is so rotated, the stylet is locked to the cannula 32.

Assembly 30 is inserted into the patient to establish a portal to the tissue on which the procedure is to be performed. The practitioner uses conventional means to insert the assembly 30. These include the application of simple hand force along the axis of cannula body 34 or the application of hand force while rotating the assembly so the tip 112 rotates. Alternatively, the practitioner may use a mallet like device to apply the force needed to advance the assembly towards the tissue.

Regardless of how the force is applied to the assembly 30, the cannula and stylet are often exposed to different resistive forces. For example, when an axial force is applied to the assembly, the stylet may be exposed to a resistive force greater than that to which the cannula is exposed. When the assembly 30 is in this state, the stylet 110 tends to resist advancement more than the cannula resists advancement. Should this event occur, stylet tab 132 abuts the inner surface of the cannula handle that defines the proximal end of notch 88. Simultaneously, stylet tab 144 abuts the inner surface of the cannula handle that defines the proximal side of notch 66. As a result of these tabs-against-surfaces abutment, the stylet shaft 114 is blocked from retracting distally out of cannula body 34. Stylet 110 is forced into advancing in unison with the cannula 32.

It should thus be appreciated that stylet tabs 132 and 144 and the complementary notch-defining portions of the cannula serve as components of the lock assembly of the cannula of this invention.

As mentioned above, during the advancement process, the practitioner may want to rotate the assembly 30. This rotation is performed to use tip 112 as drill bit for removing the tissue that impedes the advancement of the assembly. The practitioner by grasping the cannula handle 40 is able to rotate the tip counterclockwise as represented by curved arrow 152 in FIG. 8. When the assembly is so rotated, since the stylet is subjected to more torsional resistance than the cannula, the rotation of the stylet can start to lag the rotation of the cannula. When this event occurs, tab 132 abuts the surface internal to web 84 that defines the end of notch 88. Simultaneously, tab 144 abuts surface 68 internal to cannula handle web 64. These tabs-against-surfaces abutments force the stylet to rotating in unison with the cannula.

The practitioner may also rotate assembly 30 clockwise, in the direction of arrow 154 of FIG. 8. Again, owing to different torsional loading, the stylet 110 may start to lag the rotation of the cannula 32. When this event occurs, surface 94 internal to cannula handle web 84 presses against stylet handle tab 134. This action may start to force tab 134 out of slot 92. Should this event start to occur, arm outer section 138, will be displaced. More particularly, the arm outer section will start to move towards handle head 122. The movement of the arm outer section 138 is blocked by the abutment of the arm outer section against surface 55 of stop 54 integral with cannula handle 40. Since the arm 124 is blocked from movement, tab 134 likewise does not retract out of slot 92. This means the clockwise rotation of the cannula handle 40 forces the stylet into the same rotation. Thus, regardless the direction in which force is applied to the cannula handle, the lock assembly of this invention holds the stylet to the cannula so the two components rotate in unison.

Tab 134 and the complementary notch 92 defining portion of the cannula handle 40 thus functions as complementary components of the lock assembly of cannula assembly 30. Again, stop 54 prevents unintended movement of the flexible arm. Accordingly the stop 54 and the portion of the arm that abuts the stop are also complementary components of the lock assembly.

Once the cannula is in the positioned required to continue the procedure, it is necessary to withdraw the stylet 110. The lock assembly is unlatched by applying finger force to the outer face of the arm outer section 138. This finger force causes the arm to the pivot where the intermediate section 130 bends away from base 126. The location where this finger force is applied is in terms of distance is spaced more than 5 mm and typically at least 8 mm away from the axis of flexure. This means the torque applied to the arm intermediate section to induce this flexure is greater than if the same amount of linear force was applied closer to this flexure axis. Thus, finger tip force enough is sufficient to cause the desired flexure of arm 124. As a consequence of the flexure of the arm intermediate and outer sections 130 and 138, respectively, the free end of the outer section rotates past stop 54. (Counterclockwise in FIG. 8.) Stop 54 thus does not pose an obstacle to the flexure of the arm 124. As a result of the continued flexure of the arm, tab 134 rotates out slot 92.

Once tab 134 is clear of slot 92, the continued application of finger force against the arm outer section 138 is transferred from the arm 124 and shoulder 123 to head 122. The force causes the head 122, and, by extension, stylet shaft 114 to rotate. The force applied to the stylet shaft is typically sufficient to break the tip 112 free of the bone in which the tip is embedded. This force is also typically sufficient to break loose tissue that may be disposed between the shaft 114 and the wall internal to the cannula. This tissue, which often consists of bone fragments, if not broken free from between the shaft and cannula, can impede the withdrawal of the shaft from the cannula. Once the tip is freed from the bone, it is a simple matter to withdraw the stylet from the cannula 32. Cannula bore 36 then functions as the portal through which the tissue adjacent the distal end of the cannula can be accessed.

A further feature of this invention is that the surface of the arm outer section 138 against which finger force is applied is typically at least 1.2 cm and, more preferably, at least 1.5 cm away from the longitudinal axis that extends through stylet shaft 114 and head 122. This means the torque developed when a finger is pressed against arm 124 is more than is developed when the same amount of finger force is applied to the head. (When finger force is applied to the head, the force is applied at a location typically 1 cm or less from the longitudinal axis.) Relative to applying finger force to the head, this means that when this invention is used, for the same amount of finger force, more force is transferred through the shaft 114 to the tip 112. This means more force is available to break the tip 112 out of the bone in which the tip is embedded.

It should likewise be understood that the torsional force applied to the stylet to break the tip away from the bone is typically not transferred to the cannula body 36. The essential elimination of this force transfer results in a like elimination that this force transfer can result in the unintended dislocation of the cannula body from the position in which was inserted by the practitioner.

The above is directed to a specific version of the invention. Alternative versions of the invention may have features different from what has been described.

For example, the structure of the lock assembly may be different from what has been described. Thus, the lock assembly of this invention may not always have a flexible arm with three sections wherein the adjacent sections of the arm are angled from each other. In some versions of the invention, the arm may be a single piece planar structure or only have two sections that are angled from each other. Similarly, in some versions of the invention the arm may have four or more sections that are angled from each other. Likewise, the arm not always have one or more planar sections. In some versions of the invention, the arm may be circular or spiral in shape. Likewise, in some versions of the invention, the arm may extend directly from the head of the stylet handle. In these versions of the invention, it may not be necessary to provide the stylet with a component similar to shoulder 123.

Likewise, there is no requirement that, in all versions of the invention, the moveable component of the lock assembly, the arm, be attached to the stylet. In an alternative version of the invention, the arm may be flexibly attached to a static portion of the cannula.

Further, in some versions of the invention, it may not be necessary to provide a stop that blocks unintended flexure of the arm.

In some versions of the invention two arms may extend outwardly from the head 122 of the stylet handle. Both arms may be flexibly attached to the head. Each arm may have its own lock feature for engaging the cannula handle so as to prevent rotation of the stylet. To free the stylet from the cannula, it is necessary to flex both arms in order to disengage each arm lock feature from the complementary lock feature integral with the cannula handle.

The structure of the cannula and stylet may different from what has been described. In this regard it would typically be the structure of the stylet that would be different from the described version of the invention. Specifically, there is no requirement that in all versions of the invention the stylet shaft be a solid rod. In alternative versions of the invention the stylet shaft may have features that make it possible to perform a procedure other than penetrate tissue with the shaft. For example, the shaft may have a bore. This bore would function as a conduit through which an instrument or an agent could be introduced into the tissue adjacent the distal end of the assembly 30. Alternatively, the stylet could be provided with a retractable blade. In these versions of the invention, when the distal end of the assembly is located at the site at which the procedure is to be performed the blade is extended away from the shaft and the assembly is rotated. The rotation of the blade serves to create a cavity in the tissue in which the assembly 30 is inserted. In these versions of the invention, integral with the cannula body are features or components that facilitate the selective extension and retraction of the blade.

The shapes of the components may likewise be different from what has been described. Thus in some versions of the invention the stop may be in the form a rectangle, or a circular pin. The complementary locking features on the arm and cannula head that when engaged, prevent the rotation of the rotation of the stylet to a cannula may vary from the disclosed tab-in-slot assembly. These features could for example be a pin-in-bore or consist of a two sets of interlocking teeth. In some versions of the invention the locking unit may prevent the rotation of the stylet in both the clockwise and counterclockwise directions relative to the cannula.

Similarly in versions of the invention where the arm and cannula locking unit prevents rotation of the stylet in one direction relative to the cannula a second locking unit that consists of an assembly other than a tab-in-slot arrangement may prevent the rotation of the stylet in the opposed direction relative to the cannula. Likewise locking units other than the disclosed tab in slot arrangement may prevent the longitudinal movement of the stylet relative to the cannula. Thus, the invention may have three locking units: the first locking unit, the arm and cannula locking unit that selectively prevents rotation of the stylet relative to the cannula in a first direction; a second locking unit that selectively prevents rotation of the stylet relative to the cannula in a second direction; and a third locking unit that selectively prevents the longitudinal displacement of the stylet relative to the cannula.

Further, while the described version of the invention as being used for medical and surgical procedures, use of the invention is not limited to surgery. For example, it may be useful to install the lock assembly of this invention to other multi-component devices where it is desirable to releasably lock two components together so that, if the locked components are exposed to very different axial or torsional forces, the components remain fixed together.

Accordingly, it is an object of the appended claims to cover all such variations and modifications the cover the true scope and spirit of this invention.

What is claimed is:

1. A needle assembly comprising:
a cannula comprising a tube with a bore, the tube having opposed proximal and distal ends, and a handle attached to the proximal end of the tube and comprising a locking feature;
a stylet comprising a shaft dimensioned to be removably received in the bore of the tube to define a longitudinal axis of the cannula, the shaft having opposed proximal and distal ends, a handle attached to the proximal end of the shaft, and an arm coupled to the stylet handle and comprising a locking feature with the arm configured to receive a digit force; and
a lock assembly for releasably connecting the stylet handle to the cannula handle, said lock assembly comprising the complementary locking features on the cannula handle and the arm so that, when engaged, the stylet handle and the cannula handle are configured to be rotated in unison about the longitudinal axis, wherein said arm is flexibly attached to the stylet handle so as to be moved from a first position in which the complementary locking features are engaged and a second position in which the locking feature of the arm moves towards the stylet handle with flexure of the arm to space apart the complementary locking features from each other so as to allow the rotation of the stylet handle relative to the cannula handle and removal of the shaft of the stylet from the bore of the tube.

2. The needle assembly of claim 1, wherein said complementary locking features further comprises:
a first tab that extends outwardly from said arm; and
a slot formed in the cannula handle, the slot dimensioned to receive said first tab, said first tab and said slot collectively shaped so that seating of said first tab in slot lock the stylet handle from rotation.

3. The needle assembly of claim 1, wherein said lock assembly further comprises a second set of complementary locking features that, when engaged, prevents longitudinal movement of the stylet handle relative to the cannula handle.

4. The needle assembly of claim 3, wherein said second set of complementary locking features comprises at least one second tab that extends from one of the stylet handle or the cannula handle, and a notch formed in the other one of the cannula handle or the stylet handle for receiving said at least one second tab.

5. The needle assembly of claim 1, wherein the stylet handle and the cannula handle are configured to be rotated in unison in a first direction about the longitudinal axis when the complementary locking features are engaged, wherein the cannula handle comprises a stop configured to block movement of the arm, thereby preventing disengagement of the complementary locking features when the stylet is rotated in a second direction, opposite the first direction, about the longitudinal axis.

6. The needle assembly of claim 5, wherein the stop is positioned adjacent the arm when the when the stylet handle is positioned adjacent the cannula handle such that flexure of the arm moves the arm past the stop.

7. The needle assembly of claim 1, wherein:
said stylet handle is formed with a head; and
said arm comprises first and second segments angled relative to one another.

8. The needle assembly of claim 1, wherein said arm extending from the stylet handle is a singular arm.

9. The needle assembly of claim 1, wherein the arm is configured to flex about an axis parallel to the longitudinal axis.

10. A method of disengaging a stylet removably received within a bore of a cannula of a needle assembly with the bore defining a longitudinal axis of the cannula, wherein each of the stylet and the cannula include a locking unit feature for releasably coupling a stylet handle secured to the stylet and a cannula handle secured to the cannula, said method comprising:
applying a force to an arm flexibly attached to and extending outwardly from a head of the stylet handle so as to cause flexure of the arm to move the arm from a first position in which (i) the complementary locking unit features are engaged to prevent rotation of the stylet handle relative to the cannula handle about a longitudinal axis of the cannula handle to a second position in which the locking feature on the arm of the stylet handle moves towards the head of the stylet handle with the flexure of the arm to space apart the complementary locking unit features from each other; and rotating the stylet handle relative to the cannula handle with the arm in the second position.

11. The method of claim 10, wherein the locking unit feature of the stylet handle includes a first tab, wherein the step of applying the force to the arm further comprises applying the force to an outer section of the arm coupled at an angle to an intermediate section of the arm such that the flexure of the arm results in inward movement of the first tab as the arm is moved to the second position.

12. The method of claim 11, wherein the force applied to the outer section of the arm is substantially perpendicular to the inward movement of the first tab.

13. The method of claim 10, wherein the locking unit features of the stylet and the cannula are first locking unit features, wherein each of the stylet and the cannula further include second locking unit features preventing longitudinal movement of the stylet handle relative to the cannula handle in the first position, said method further comprising simultaneously disengaging the first and second locking unit features.

14. The method of claim 10, wherein the cannula handle includes a stop preventing inward movement of the arm, said method further comprising moving the arm past the stop, thereby permitting the flexure of the arm and inward movement of the arm from the first position to the second position.

15. The method of claim 14, wherein the arm includes an outer section, and an intermediate section coupled to outer section with the locking unit features of the stylet handle coupled to the intermediate section, said method further comprising applying the force to the outer section to move the outer section of the arm past the stop and flex the arm once the outer section is past the stop.

16. The method of claim 10, wherein the step of rotating the stylet handle relative to the cannula handle further comprises applying an additional force to the arm to provide a torque to the stylet handle while a position of the cannula handle is maintained.

17. The method of claim 10, further comprising removing the stylet from the bore of the cannula.

18. A needle assembly comprising:
a cannula comprising a tube with a bore, the tube having opposed proximal and distal ends defining a longitudinal axis, a handle attached to the proximal end of the tube;
a stylet comprising a shaft dimensioned to be removably received in the bore of the tube, the shaft having opposed proximal and distal ends, a handle attached to the proximal end of the shaft so that when the stylet shaft is in the bore of the tube when the stylet handle is positioned adjacent the cannula handle, and an arm comprising an intermediate section extending from the handle, and an outer section extending from the intermediate section and defining an outer end of the arm; and
a lock assembly for releasably connecting the stylet handle to the cannula handle so that the stylet handle selectively rotates in unison with the cannula handle about the longitudinal axis, the lock assembly comprising complementary locking features on the cannula handle and the stylet handle so that, when engaged, the stylet handle relative to the cannula handle are configured to be rotated in unison about the longitudinal axis, wherein the locking feature of the stylet handle extends outwardly from the intermediate section of the arm,
wherein the outer section of the arm is arranged to receive a digit force to flex at least the intermediate section and the outer section inward towards the handle such that the complementary locking features disengage so as to allow rotation of the stylet handle relative to the cannula handle and removal of the shaft of the stylet from the bore of the cannula.

19. The needle assembly of claim 18, wherein the cannula handle further comprises a stop positioned adjacent the outer section of the arm when the stylet handle is positioned adjacent the cannula handle, the stop configured to block movement of the arm, preventing disengagement of the locking features and rotation of the stylet handle relative to the cannula handle, wherein the outer section of the arm is configured to flex and move past the stop.

20. The needle assembly of claim 18, wherein the lock assembly further comprises a tab that extends from the stylet handle, and a notch formed in the cannula handle for receiving the tab such that, when the tab and the notch are engaged, longitudinal movement of the stylet handle relative to the cannula handle is prevented.

* * * * *